(12) United States Patent
Chen et al.

(10) Patent No.: US 7,553,991 B1
(45) Date of Patent: Jun. 30, 2009

(54) PROCESS FOR PRODUCING CARBOXYLIC ACID ANHYDRIDES

(75) Inventors: Chi He Chen, Renwu Township, Kaohsiung County (TW); Ching Liang Tu, Sinshih Township, Tainan County (TW); Chia Hui Shen, Gangshan Township, Kaohsiung County (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 12/150,524

(22) Filed: Apr. 29, 2008

(30) Foreign Application Priority Data

Jan. 7, 2008 (TW) .............................. 97100527 A

(51) Int. Cl.
  *C07C 51/56* (2006.01)
(52) U.S. Cl. ..................................... 562/891
(58) Field of Classification Search ........ None
  See application file for complete search history.

(56) References Cited

U.S. PATENT DOCUMENTS 4,115,444 A * 9/1978 Rizkalla ..................... 562/891
5,939,585 A * 8/1999 Ditzel et al. ................. 562/519

FOREIGN PATENT DOCUMENTS

| CN | 1778468 A | 5/2006 |
| CN | 1876239 A | 12/2006 |
| EP | 0 391 680 A1 | 10/1990 |
| EP | 0 153 834 B2 | 6/1993 |

* cited by examiner

Primary Examiner—Paul A Zucker

(74) *Attorney, Agent, or Firm*—Clifford W. Browning; Krieg DeVault LLP

(57) ABSTRACT

The present invention relates to a process for producing carboxylic acid anhydrides, in which a carboxylic acid ester, derived from an alcohol and a carboxylic acid, and carbon monoxide containing a small amount of hydrogen are used as raw materials and subjected to a carbonylation reaction in a liquid reaction medium in the presence of a Group VIII B catalyst to produce a carboxylic acid anhydride. The reaction medium comprises the Group VIII B catalyst, an organic halide, the carboxylic acid ester, an alkali metal salt, at least one organic promoter, the carboxylic acid anhydride and the carboxylic acid, wherein the organic promoter is selected from at least one of the following structural forms (I), (II) and (III). According to the process of the present invention, the reaction rate of the carbonylation reaction is increased by the use of the specified organic promoters.

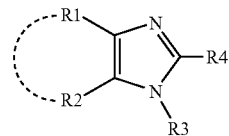

(I)

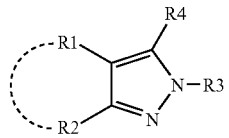

(II)

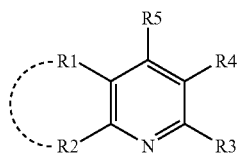

(III)

18 Claims, No Drawings

PROCESS FOR PRODUCING CARBOXYLIC ACID ANHYDRIDES

FIELD OF THE INVENTION

The present invention relates to a process for producing carboxylic acid anhydrides by way of the carbonylation reaction of a derivative from an alcohol and a carboxylic acid with carbon monoxide, and in particular, a process for producing acetic anhydride by way of the carbonylation reaction of methyl acetate with carbon monoxide, which is characterized in that in a catalytic system containing a Group VIII B catalyst, one or more organic compounds are added as the promoter to increase the reaction rate, so that the operational range for the reaction can be extended, enabling the reaction to be carried out under milder conditions.

BACKGROUND TO THE INVENTION

Acetic anhydride is a well-known raw material widely used in the chemical industry, which is mainly used for producing chemicals such as cellulose acetate and is an important raw material for synthesizing medicines, flavors, dyes, etc. There are currently three industrial processes for producing acetic anhydride, including the ketene process, the acetaldehyde oxidation process and the methyl acetate carbonylation process. Among these processes, the ketene process, which belongs to an old-fashioned process and is small in scale, is adopted by many manufacturers and is thus predominant; however, the largest-scale single process for commercially producing acetic anhydride at present is the methyl acetate carbonylation process due to the high energy consuming and other drawbacks of the ketene process.

The ketene process is carried out by dissociating one water molecule or methane from the raw material, acetic acid or acetone, at a high temperature to form ketene, which then reacts with acetic acid to form acetic anhydride. The reaction temperature of this process is up to 750° C.; therefore, this process will gradually go out of use in the future for its high energy-consuming demand.

The acetaldehyde oxidation process is carried out by using metals such as manganese, cobalt, nickel, copper, etc. as the catalyst and oxidizing acetaldehyde into peracetic acid, which further reacts with acetaldehyde to form acetic anhydride and the by-product, water. Acetic anhydride will further be hydrolyzed into acetic acid so that the yield of acetic anhydride will be reduced. Therefore, the product of the acetaldehyde oxidation process is the mixture of acetic anhydride and acetic acid.

The methyl acetate carbonylation process for producing acetic anhydride is an expanded application of the methanol carbonylation process for producing acetic acid. The methyl acetate carbonylation process for producing acetic anhydride is carried out by reacting methyl acetate with carbon monoxide to produce acetic anhydride in the presence of the transition metal catalyst (such as rhodium, nickel, cobalt, iridium, etc.) and the iodide promoter. The difference between the methyl acetate carbonylation process and the methanol carbonylation process is the water content of the reaction solution; the reaction solution of the former has to be kept in anhydrous conditions, while the reaction solution of the latter can have any water ratio of 1~20 wt. %. Water has a great influence on the stability of the catalyst, and the high water content is advantageous to the stability of the catalyst. Therefore, the stability of the catalyst in the anhydrous system of the methyl acetate carbonylation process is a primary problem that should be overcome. In order to solve the problem, a promoter or a co-catalyst such as alkali metal, phosphonium salt, ammonium salt and transition metal catalysts can be added to promote the stability and activity of the catalytic system. In addition, the carbon monoxide feed gas in the methyl acetate carbonylation process for producing acetic anhydride must contain a small amount of hydrogen so as to maintain the activity of the rhodium catalyst.

U.S. Pat. No. 4,002,678 discloses a preparation of acetic anhydride under anhydrous conditions by using nickel and chromium as the catalyst and carbon monoxide and methyl acetate or dimethyl ether as the raw materials to carry out a carbonylation reaction in the presence of a halide and a trivalent organo-nitrogen compound or a trivalent organo-phosphorus compound. The reaction temperature is about 150° C. and the pressure is controlled within 1000 psi. The organo-nitrogen compound promoter includes 2-hydroxypyridine, 2-quinolinol, 8-quinolinol, 2,6-diaminopyridine, etc. However, according to the disclosure of this patent, the reaction requires a time of several hours to several tens hours, depending on the conditions, and the conversion rate is substantially low.

U.S. Pat. No. 4,115,444 discloses a process for preparing acetic anhydride, in which a Group VIII noble metal is used as the catalyst, together with multiple promoters comprising at least one metal of Groups IVB, VB, and VIB or a non-noble metal of Group VIII or their compounds and a trivalent organo-nitrogen compound or a trivalent organo-phosphorus compound. The catalyst can be rhodium or iridium, the metal promoter can be iron, cobalt, nickel, chromium, etc., and the organo-nitrogen compound promoter includes an amine, an imidazole, an imide, an amide, an oxime, etc., of which triethylamine, methyl imidazole, 2,6-dimethylpyridine, etc. are given in the examples. This patent discloses the performance of multiple promoters of iron, cobalt, nickel and chromium; however, the influence of alkali metal iodine salts and organic promoters on the reaction rate is never disclosed.

U.S. Pat. No. 4,430,273 discloses a process for making acetic anhydride, wherein methyl acetate or dimethylether as the raw material is reacted with carbon monoxide under anhydrous conditions, at temperatures of 77~302° C. and under pressures of 1~300 bar in the presence of a Group VIII noble metal as the catalyst, while at least one heterocyclic aromatic compound (a quaternary nitrogen atom) is added as the promoter. The added heterocyclic aromatic compounds as given in the examples are aromatic iodine salts and are mostly with simple structures such as N-methylpyridine, N-methylimidazole, etc. However, this patent describes neither what structures of heterocyclic aromatic compounds are effective and how much performance they improve, nor the influence of addition of metal iodide salts.

U.S. Pat. No. 4,536,354 discloses a process for preparing carboxylic acid anhydrides, in which nickel is used as the catalyst and a compound having the following structure is used as the promoter:

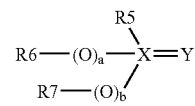

In the above structural formula, X represents phosphorus, arsenic or antimony, Y represents oxygen, sulphur or selenium, a and b are 0 or 1, R5 represents hydrogen or a substituted or non-substituted hydrocarbon group, and R6 and R7 represent a substituted or non-substituted hydrocarbon group;

or a and b are 0, R5 represents hydrogen or a substituted or non-substituted hydrocarbon group, and R6 and R7 form a heterocyclic group. In the examples of this patent, a triphenylphosphine oxide as the promoter, which is mainly a phosphorus-containing oxide of the above structure, is disclosed. However, this patent does not disclose the difference in performance between the organic promoters and the aromatic organic additives.

U.S. Pat. No. 4,544,511 discloses a process for producing acetic anhydride by using nickel or a nickel compound as the catalyst together with a metal co-catalyst selected from Groups IA, IIA, IIIB or IVB, and carbon monoxide, methyl acetate or dimethyl ether as the raw materials to carry out a carbonylation reaction at temperatures of 100~250° C. and CO partial pressures of 3~150 kg/cm² in the presence of a halide (bromide or iodide) and at least one trivalent organic nitrogen group promoter. There are three kinds of organic promoters disclosed in this patent:

(I) Compounds of trivalent nitrogen group elements represented by the following formulae:

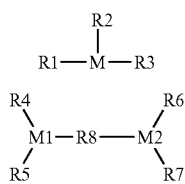

wherein the formula (2), in which M is N, P, As or Sb, includes triethyl amine, triphenyl amine, N,N-diethyl glycine, etc., and the formula (3) includes N-methyl-2-pyrrodinone, triethylenediamine, etc. when M1 and M2 are N; (II) Hetero cyclic compounds such as picoline, 2,4-lutidine, 2,6-lutidine, 2-hydroxypyridine, 4-picolyamine, 3-pyridinemethanol, picoline-N-oxide, 2-carboxyquinoline, etc.; and (III) Compounds of pentavalent nitrogen group elements.

Although the organic compounds as mentioned in the above patent all need to be used with a metal co-catalyst such as an iodide containing lithium, Tin, aluminum, etc., yet there is no disclosure of the improved performance of the reaction after the addition of organic promoters to the metal iodides that have been contained in the original reaction composition.

EP 0153834 discloses a stabilizer selected from a thiol or an imidazole for preventing the precipitation of the rhodium catalyst in a water-containing carbonylation process. The structure of the imidazole as used in this patent is as below:

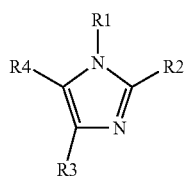

in which R1~R4 are each independently selected from hydrogen, alkyl, aryl, cycloalkyl or alkaryl hydrocarbyl radicals, and the preferred example is N-methylimidazole. However, this patent does not disclose the influence of the catalyst stabilizer on the reaction rate under low water content conditions or even anhydrous conditions, and the examples of applying the catalyst stabilizer in an acetic anhydrides process. Also, the catalyst stabilizer is liable to, with rhodium, form a hardly soluble complex, which will be precipitated from the solution.

EP 0391680 A1 discloses a process for preparing carboxylic acids by using an alcohol or an ester thereof under water-containing conditions and using a quaternary ammonium iodide as a stabilizer of the rhodium catalyst. The structure of the quaternary ammonium iodide is shown as below:

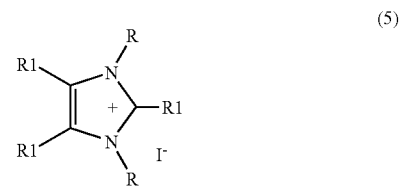

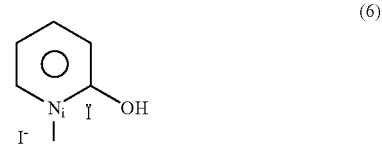

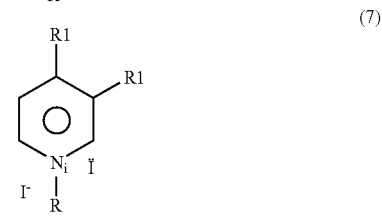

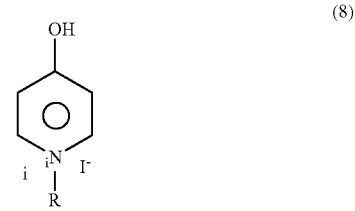

in which R and R1 are independently selected from hydrogen or an alkyl group having 1~20 carbon atoms and at least one R1 is not hydrogen, and the preferred example is 2-ethyl-4-methylimidazole, 4-methylimidazole, 4-ethylpyridine, 4-t-butylpyridine and 3,4-lutidine. However, although this patent discloses the stabilizing effect of the iodide stabilizer but does not investigate the influence of the acetic anhydride process under anhydrous conditions on the reaction rate.

CN 1876239A and CN 1778468A both disclose a catalytic system for the synthesis of the carbonyl group of methyl acetate to an acid anhydride by using a rhodium compound as the catalyst and different contents of alkyl iodides, hetero-polyacid salts and alkali metal iodine salts as the promoter. The performance of this catalytic system is improved by the synergistic effect of the hetero-polyacid salts, which belong to inorganic compound additives, and the catalyst. However, these patents do not investigate the performance of addition of organic additives.

U.S. Pat. No. 5,298,586 discloses a process for the production of carboxylic acid anhydrides by using an alkyl ester or an alkyl ether as the raw material to carry out the rhodium-catalyzed carbonylation reaction under anhydrous conditions, in which an organic promoter is added to improve the solubility and stability of the rhodium catalysts. The structure of the organic promoter as disclosed in this patent is shown as below:

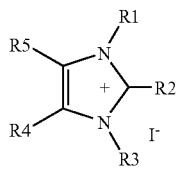

(9)

including 1,3-dialkyl-4-methylimidazolium iodide, 1,3-dialkyl-2,4,5-trimethylimidazoliumiodide, etc., and the preferred promoters are 1,3,4-trimethylimidazolium iodide and 1,2,3,4,5-pentamethylimidazolium iodide. However, this patent does not investigate the influence of addition of organic promoters on the space-time yield of acetic anhydrides.

Therefore, there is still a demand for a process for producing acetic anhydrides under severe carbonylation conditions which can effectively stabilize the rhodium catalyst and maintain a high reaction rate at the same time.

SUMMARY OF THE INVENTION

The main object of the present invention is to produce carboxylic acid anhydrides under anhydrous conditions, which can also increase the reaction rate.

In order to achieve the aforementioned and other objects, the present invention provides a process for producing carboxylic acid anhydrides, in which a carboxylic acid ester, derived from an alcohol and a carboxylic acid, and carbon monoxide containing a small amount of hydrogen are used as raw materials and subjected to a carbonylation reaction in a liquid reaction medium in the presence of a Group VIII B catalyst to produce a carboxylic acid anhydride. The reaction medium comprises the Group VIII B catalyst, an organic halide, the carboxylic acid ester, an alkali metal salt, at least one organic promoter, the carboxylic acid anhydride and the carboxylic acid, wherein the organic promoter is selected from at least one of the following structural forms (I), (II) and (III):

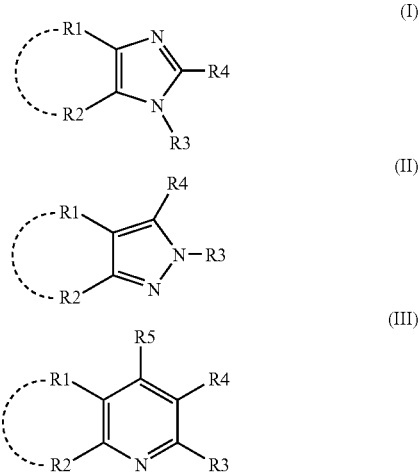

In the above structural formulae, R1~R5 can be the same or different and are independently selected from the group consisting of hydrogen atom, $C_{1-12}$ alkyl group, $C_{3-12}$ cycloalkyl group, $C_{6-20}$ aryl group, $C_{7-20}$ alkylaryl group, $C_{7-20}$ arylalkyl group, hydroxyl group, $C_{1-12}$ hydroxyalkyl group (—R—OH), carboxyl group, $C_{2-12}$ carboxyalkyl group (—R—COOH), $C_{2-12}$ alkoxyformyl group (—CO—OR), $C_{2-12}$ alkylacyloxy group (—O—CO—R), $C_{1-12}$ aminoformyl group (—CO—NRR'), $C_{2-12}$ alkylamido group (—NR—CO—R) $C_{1-12}$ alkylamino group (—N—RR'), $C_{3-12}$ cycloalkylamino group, $C_{1-12}$ aminoalkyl group (—R—NRR'), $C_{4-12}$ cycloaminoalkyl group, $C_{2-12}$ alkylacyl group (—CO—R), $C_{2-12}$ cycloalkylacyl group, $C_{1-12}$ amidoalkyl group (—R—CO—NRR'), $C_{1-2}$ imido group (—N(CO—R)$_2$), $C_{1-12}$ imidoalkyl group (—R—N(CO—R)$_2$), $C_{1-12}$ alkoxy group (—O—R), $C_{2-12}$ cycloalkoxy group, $C_{1-12}$ amino acid alkyl group and R1 and R2 can be coupled to form an aromatic ring, a heteroaromatic ring or a non-aromatic ring.

In the process for producing carboxylic acid anhydrides according to the present invention, a carboxylic acid ester, derived from an alcohol and a carboxylic acid, and carbon monoxide containing a small amount of hydrogen are fed into a reaction vessel and subjected to a carbonylation reaction in the presence of a catalyst (for example, rhodium (Rh)) so as to produce a carboxylic acid anhydride. The alcohol is an aliphatic alcohol compound having 1~6 carbon atoms, and the carboxylic acid is a carboxylic acid having 1~6 carbon atoms. According to the process of the present invention, the carbon monoxide gas for the carbonylation reaction contains an adequate amount of hydrogen, which can facilitate the maintenance of the activity of the Rh catalyst; preferably, the carbon monoxide feed gas contains hydrogen at a concentration of 10% or below. In the liquid reaction medium, 300~3000 ppm of the Rh catalyst, 5~30 wt. % of the organic halide, 1~15 wt. % of the alkali metal salt, a total of 0.5~20 wt. % of the organic promoter(s), and the carboxylic acid ester, the carboxylic acid anhydride, the carboxylic acid and a small amount of impurities are usually contained. The carbonylation reaction can be carried out at a temperature of between 160~240° C. and at a controlled carbon monoxide pressure of between 20~60 kg/cm$^2$.

Compared with the aforementioned prior art, the process of the present invention is using different organic promoters, which can form a stable complex compound with the Rh catalyst and has the effect of increasing the carbonylation reaction rate. The addition of alkali metal iodine salts in the conventional anhydrous carbonylation process has the effect of stabilizing rhodium; however, the sequent purification, separation and deiodination processes for the product have resulted in much trouble. The addition of organic promoters can increase the carbonylation reaction rate and reduce the sequent operation of the equipment for the deiodination process, which has the advantage of reducing the cost of purifying the acetic anhydride product.

DESCRIPTION OF PREFERRED EMBODIMENTS

The features and effects of the present invention will be further explained with reference to the preferred embodiments below, which are, however, not intended to restrict the scope of the present invention.

The present invention may be operated as a batch process, in which the equipment as used mainly includes, for example, a 1-liter reactor and a carbon monoxide storage tank both made of anticorrosive materials. The reactor itself is provided with a speed-change motor capable of controlling the rotational speed, which can be appropriately adjusted so as to maintain a vapor/liquid well-mixing effect. The inside and the outside of the reactor are provided with a cooling coil and an electrically heating plate, respectively, so as to control and maintain a stable reaction temperature. A pressure control valve is provided between the reactor and the hydrogen and carbon monoxide storage tanks so as to maintain and control the pressure of the main reactor.

One preferred embodiment of the present invention is to produce acetic anhydride by carrying out the carbonylation reaction of methyl acetate with carbon monoxide containing a small amount of hydrogen in the reactor. The reaction medium in the reactor carrying out the carbonylation reaction is maintained to comprise a Group VIII B catalyst such as, for example, rhodium; a carboxylic ester derived from an alcohol and a carboxylic acid such as, for example, methyl acetate, or an ether derived from an alcohol compound such as, for example, dimethyl ether; an organic halide corresponding to the raw material of alcohol, such as, for example, methyl iodide; an alkali metal salt such as, for example, lithium iodide; a carboxylic acid anhydride such as, for example, acetic anhydride; a carboxylic acid such as, for example, acetic acid; and at least one organic promoter.

The carbon monoxide feed gas in the carbonylation process contains an adequate amount of hydrogen, which can maintain the activity of the Rh catalyst. Preferably, the carbon monoxide feed gas contains hydrogen at a concentration of 10% or below. In the liquid reaction medium, 300~3000 ppm of the Rh catalyst, 5~30 wt. % of organic halide, 1~15 wt. % of alkali metal salt, a total of 0.5~20 wt. % of organic promoter(s), and the carboxylic acid ester, carboxylic acid anhydride, carboxylic acid and a small amount of impurities are usually contained. The carbonylation reaction can be carried out under the condition of temperatures of 160~240° C. and CO controlled pressures of 20~60 kg/cm$^2$.

Alternatively, the present invention is operated as a continuous process. Another preferred embodiment of the present invention is to continuously feed the raw material of methyl acetate, together with carbon monoxide containing a small amount of hydrogen, into the carbonylation reactor and react methyl acetate with carbon monoxide so as to form acetic anhydride. The liquid reaction medium in the reactor comprises the Rh catalyst, methyl acetate, acetic acid, acetic anhydride, methyl iodide, an alkali metal salt and at least one organic promoter. Corresponding to the continuously feeding reactor, the reaction product effluent comprises the product of acetic anhydride and the unreacted methyl acetate, acetic acid, methyl iodide, Rh catalyst, alkali metal salt and organic promoter. The liquid reaction product is continuously outputted to a flash tank (or an evaporator), the light constituents of the liquid reaction product are evaporated and discharged from the top of the flash tank to the purifying zone to further separate acetic acid and acetic anhydride, and the Rh catalyst and other heavy constituents at the bottom of the flash tank are reflowed to the reactor. After the product of acetic anhydride is separated in the purifying zone, acetic acid and other constituents (including methyl iodide, methyl acetate, etc.) are reflowed to the reactor. During the reaction process, methyl iodide, the alkali metal salt and the organic promoter will not be consumed but are continuously circulated from the flash tank or the purifying zone to the reactor. If necessary, persons skilled in the art can consider adjusting the contents of the constituents of the reaction medium in accordance with the real operation situation.

Comparative Example 1

In this comparative example, a batch process without adding the promoter of the present invention was used, as a comparative experiment, to carry out the carbonylation reaction. The following constituents with specified amounts were fed into the reactor: 50 wt. % of methyl acetate, 25 wt. % of methyl iodide, 5 wt. % of acetic anhydride, lithium iodide (40000 ppm of Li ion), 800 ppm of the Rh catalyst, and an appropriately balanced amount of acetic acid as a solvent. The reactor into which the mixture of the aforementioned reactants had been fed was firstly pressurized with hydrogen to 1 kg/cm$^2$, and then carbon monoxide was introduced into the reactor, followed by a gradual elevation of temperature. After the set temperature for the reaction was reached, carbon monoxide was resupplied so that the inner pressure of the system reached 27 kg/cm$^2$. During the reaction, carbon monoxide kept on being resupplied with the consumption of carbon monoxide so that the pressure stably maintained 27 kg/cm$^2$. The consumption of carbon oxide was recorded and a constituent analysis was carried out by sampling so as to calculate the unit space-time yield (STY) of acetic anhydride (unit: mole/liter*hour).

Examples 1~7

Improved Performance on Reaction Rate of Acetic Anhydride (STY) by Addition of Different Organic Promoters The carbonylation reactions were carried out under the same conditions as the Comparative Example 1, except that 2 wt. % of organic promoters were added in the reaction media. The results of the Examples 1~7 and the Comparative Example 1 were recorded in Table 1, and the Comparative Example 1 was a blank experiment that no organic promoter was added. It is obvious from Table 1 that the STY values for those having the organic promoters added were all increased by 6%~20%, which shows the addition of these kinds of organic promoters according to the present invention indeed has the effect of increasing the carbonylation reaction rate.

TABLE 1

Influence of Addition of Organic Promoters on Reaction Rate

| | Content of Organic Promoter | | Temp. (° C.)/ Pressure (kg/cm$^2$) | STY value (gmol/L * hr) |
|---|---|---|---|---|
| | Reagents | (wt %) | | |
| Compar. Example 1 | | | 190/27 | 9.13 |
| Example 1 | 4-pyrrolidionpyridine | 2 | 190/27 | 9.68 |
| Example 2 | 5-amino-3-methyl-1-phenylpyrazole | 2 | 190/27 | 9.87 |
| Example 3 | 3-acetoxypyridine | 2 | 190/27 | 10.05 |
| Example 4 | 2-methylbenzimidazole | 2 | 190/27 | 10.42 |
| Example 5 | 5-amino-1,3-dimethylpyrazole | 2 | 190/27 | 10.60 |
| Example 6 | N-methylbenzimidazole | 2 | 190/27 | 10.78 |
| Example 7 | N-acetylimidazole | 2 | 190/27 | 10.78 |

Examples 8~9

Influence of Reaction Pressure and Organic Promoters on Reaction Rate

The carbonylation reactions were carried out under the same conditions as the Comparative Example 1, except that 2 wt. % of organic promoter, 5-amino-1,3-dimethylpyrazole, was added in the reaction media and the CO pressure was altered. The experimental results were recorded in Table 2. It is obvious from Table 2 that the STY values of the carbonylation reaction for those having the organic promoter added and the CO pressure increased could be increased. In other words, the increase in the reaction pressure can increase the reaction rate, which shows the addition of these kinds of organic promoters according to the present invention indeed has the effect of increasing the carbonylation reaction rate at different reaction pressures.

TABLE 2

Influence of Reaction Pressure and Organic Promoters on Reaction Rate

| Content of Organic Promoter | | Temp. | Pressure | Li+ (LiI) | STY value (gmol/ |
|---|---|---|---|---|---|
| Reagents | (wt %) | (° C.) | (kg/cm²) | (ppm) | L * hr) |
| Compar. Example 1 | | 190 | 27 | 4000 | 9.13 |
| Example 2 | 5-amino-1,3-dimethyl-pyrazole | 2 | 190 | 27 | 4000 | 10.60 |
| Example 8 | | 2 | 190 | 32 | 4000 | 11.15 |
| Example 9 | | 2 | 190 | 40 | 4000 | 11.69 |

Examples 10~11

Influence of Reaction Temperature and Organic Promoters on Reaction Rate

The carbonylation reactions were carried out under the same conditions as the Comparative Example 1, except that 2 wt. % of organic promoter, 2-methylbenzimidazole, was added in the reaction media and the reaction temperature was altered. The experimental results were recorded in Table 3. It is obvious from Table 3 that the STY values of the carbonylation reaction could still be increased by adding the organic promoter and altering the reaction temperature, which shows the addition of these kinds of organic promoters according to the present invention indeed has the effect of increasing the carbonylation reaction rate at different reaction temperatures. In addition, when the Example 11 is compared with the Comparative Example 1, it is found that the addition of these kinds of organic promoters can maintain the original reaction rate at a lower reaction temperature, which has the effect of saving energy and reducing production cost.

TABLE 3

Influence of Reaction Temperature and Organic Promoters on Reaction Rate

| Content of Organic Promoter | | Temp. | Pressure | Li+ (LiI) | STY value (gmol/ |
|---|---|---|---|---|---|
| Reagents | (wt %) | (° C.) | (kg/cm²) | (ppm) | L * hr) |
| Compar. Example 1 | | | 190 | 27 | 4000 | 9.13 |
| Example 4 | 2-methyl-benzimid-azole | 2 | 190 | 27 | 4000 | 10.42 |
| Example 10 | | 2 | 200 | 27 | 4000 | 11.33 |
| Example 11 | | 4 | 180 | 27 | 4000 | 9.87 |

Examples 12~14

Influence of Added Amount of Organic Promoters on Reaction Rate

The carbonylation reactions were carried out under the same conditions as the Comparative Example 1, except that 2 wt. %, wt. % and 6 wt. % of organic promoters, N-acetylimidazole, were added in the reaction media. The experimental results were recorded in Table 4. It is obvious from Table 4 that the STY values of the carbonylation reaction were increased synchronously with the increase in the added amount of organic promoter, which shows the carbonylation reaction rate can indeed be satisfactorily increased by the increase in the added amount of these kinds of organic promoters according to the present invention. In addition, when the Example 14 is compared with the Comparative Example 1, it is found that the addition of these kinds of organic promoters can maintain the original reaction rate with the added amount of lithium iodide reduced, which shows these kinds of organic promoters and lithium iodide have the same or even better effect of stabilizing the catalyst. Another advantage is that the used amount of lithium iodide in the process can be reduced so that the load of the deiodination process in the later stage can be reduced.

TABLE 4

Influence of Added Amount of Organic Promoters on Reaction Rate

| Content of Organic Promoter | | Temp. | Pressure | Li+ (LiI) | STY value (gmol/ |
|---|---|---|---|---|---|
| Reagents | (wt %) | (° C.) | (kg/cm²) | (ppm) | L * hr) |
| Compar. Example 1 | | | 190 | 27 | 4000 | 9.13 |
| Example 7 | N-acetyl-imidazole | 2 | 190 | 27 | 4000 | 10.78 |
| Example 12 | | 4 | 190 | 27 | 4000 | 11.33 |
| Example 13 | | 6 | 190 | 27 | 4000 | 12.06 |
| Compar. Example 2 | | | 190 | 27 | 3000 | 8.22 |
| Example 14 | N-acetyl-imidazole | 4 | 190 | 27 | 3000 | 10.96 |

While the present invention has been shown and described with reference to preferred embodiments thereof, it should not be considered as limited thereby. Various possible modifications and alterations could be conceived of by one skilled in the art to the form and the content of any particular embodiment, without departing from the scope of the present invention.

What is claimed is:

1. A process for producing carboxylic acid anhydrides, in which a carboxylic acid ester, derived from an alcohol and a carboxylic acid, and carbon monoxide containing a small amount of hydrogen are used as raw materials and subjected to a carbonylation reaction in a liquid reaction medium in the presence of a Group VIII B catalyst to produce a carboxylic acid anhydride, the reaction medium comprising the Group VIII B catalyst, an organic halide, the carboxylic acid ester, an alkali metal salt, the carboxylic acid anhydride, the carboxylic acid and at least one organic promoter selected from at least one of the following structural forms (I), (II) and (III):

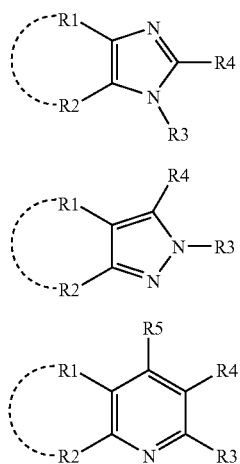

in which R1~R5 can be the same or different and are independently selected from the group consisting of hydrogen atom, $C_{1-12}$ alkyl group, $C_{3-12}$ cycloalkyl group, $C_{6-20}$ aryl group, $C_{7-20}$ alkylaryl group, $C_{7-20}$ arylalkyl group, hydroxyl group, $C_{1-12}$ hydroxyalkyl group (—R—OH), carboxyl group, $C_{2-12}$ carboxyalkyl group (—R—COOH), $C_{2-12}$ alkoxyformyl group (—CO—OR), $C_{1-12}$ alkylacyloxy group (—O—CO—R), $C_{1-12}$ aminoformyl group (—CO—NRR'), $C_{1-12}$ alkylamido group (—NR—CO—R) $C_{1-12}$ alkylamino group (—N—RR'), $C_{2-12}$ cycloalkylamino group, $C_{1-12}$ aminoalkyl group (—R—NRR'), $C_{4-12}$ cycloaminoalkyl group, $C_{2-12}$ alkylacyl group (—CO—R), $C_{1-12}$ cycloalkylacyl group, $C_{1-12}$ amidoalkyl group (—R—CO—NRR'), $C_{1-12}$ imido group (—N(CO—R)$_2$), $C_{1-12}$ imidoalkyl group (—R—N(CO—R)$_2$), $C_{1-12}$ alkoxy group (—O—R), $C_{1-12}$ cycloalkoxy group, $C_{1-12}$ amino acid alkyl group, and R1 and R2 can be coupled to form an aromatic ring, a heteroaromatic ring or a non-aromatic ring, provided that in the structural forms (I) and (III), R1~R5 are not a hydrogen atom at the same time and in the structural form (I), when R1, R2 and R4 are a hydrogen atom, R3 is not a methyl group.

2. The process according to claim 1, wherein the alcohol is an alcohol having 1~6 carbon atoms.

3. The process according to claim 1, wherein the carboxylic acid is a carboxylic acid having 1~6 carbon atoms.

4. The process according to claim 1, wherein the carboxylic acid ester is methyl acetate.

5. The process according to claim 3, wherein the carboxylic acid is acetic acid.

6. The process according to claim 1, wherein the carboxylic acid anhydride is acetic anhydride.

7. The process according to claim 1, wherein the carbonylation reaction is carried out at a temperature of between 160~240° C.

8. The process according to claim 1, wherein the carbonylation reaction is carried out at a pressure of between 20~60 kg/cm$^2$.

9. The process according to claim 1, wherein the reaction medium contains the Group VIII B catalyst at a total concentration of 300~3000 ppm.

10. The process according to claim 9, wherein the Group VIII B catalyst is at least one catalyst selected from the group consisting of rhodium, nickel, cobalt and iridium.

11. The process according to claim 1, wherein the organic halide is a methyl halide.

12. The process according to claim 11, wherein the methyl halide is methyl iodide.

13. The process according to claim 12, wherein the reaction medium contains 5~30 wt. % of methyl iodide.

14. The process according to claim 1, wherein the carbon monoxide feed gas contains hydrogen at a concentration of 0.1~0%.

15. The process according to claim 1, wherein the alkali metal salt is a Group IA/IIA iodide salt.

16. The process according to claim 15, wherein the reaction medium contains 500~8000 ppm of Group IA/IIA metal ions for providing the corresponding content of iodine ions.

17. The process according to claim 1, wherein the at least one organic promoter is added at a total content of 0.5~20 wt. %.

18. The process according to claim 1, wherein the at least one organic promoter is selected from the group consisting of 2-aminobenzimidazole, 2-methylbenzimidazole, 3-acetoxypyridine, N-methylbenzimidazole, N-acetylimidazole, 1-phenylpyrazole, 1,3,5-trimethylpyrazole, 5-amino-3-methyl-1-phenylpyrazole, 5-amino-1,3-dimethylpyrazole, 4-pyrrolidinopyridine.

* * * * *